United States Patent [19]

Müller-Gliemann et al.

[11] Patent Number: 5,459,156
[45] Date of Patent: Oct. 17, 1995

[54] IMIDAZOLYL-SUBSTITUTED PHENYLACETIC ACID PROLINAMIDES

[75] Inventors: Matthias Müller-Gliemann, Solingen; Jürgen Dressel, Radevormwald; Peter Fey, Wuppertal; Rudolf H. Hanko, Düsseldorf; Walter Hübsch, Wuppertal; Thomas Krämer, Wuppertal; Ulrich E. Müller, Wuppertal; Martin Beuck, Erkrath; Stanislav Kazda, Wuppertal; Stefan Wohlfeil, Hilden; Andreas Knorr, Erkrath; Johannes-Peter Stasch, Solingen; Siegfried Zaiss, Wuppertal; all of Germany

[73] Assignee: Bayer Aktiengesellschaft, Leverkusen, Germany

[21] Appl. No.: 188,615

[22] Filed: Jan. 27, 1994

[30] Foreign Application Priority Data

Feb. 3, 1993 [DE] Germany ............. 43 02 957.4

[51] Int. Cl.⁶ ............. A61K 31/415; C07D 403/10
[52] U.S. Cl. ............. 514/397; 548/314.7
[58] Field of Search ............. 514/397; 548/314.7

[56] References Cited

U.S. PATENT DOCUMENTS

| 5,128,355 | 7/1992 | Carini et al. | 514/381 |
|---|---|---|---|
| 5,138,069 | 8/1992 | Carini et al. | 548/253 |
| 5,153,197 | 10/1992 | Carini et al. | 514/255 |
| 5,155,118 | 10/1992 | Carini et al. | 514/381 |

FOREIGN PATENT DOCUMENTS

| 0010347 | 4/1980 | European Pat. Off. . |
|---|---|---|
| 0573271 | 12/1993 | European Pat. Off. . |
| WO9112002 | 8/1991 | WIPO . |

OTHER PUBLICATIONS

J. Med. Chem., 1990, vol. 33, pp. 1312–1329; "The Discovery of Potent Non-peptide Angiotensin II Receptor . . . ", J. V. Duncia et al.

The Journal of Cell Biology, vol. 50, 1971, pp. 172–186.

*Primary Examiner*—Patricia L. Morris
*Attorney, Agent, or Firm*—Sprung Horn Kramer & Woods

[57] ABSTRACT

Imidazolyl-substituted phenylacetic acid prolinamides are prepared by reacting corresponding imidazolyl-substituted phenylacetic acids with prolines. The imidazolyl-substituted phenylacetic acid prolinamides can be used as active compounds in medicaments, preferably for the treatment of hypertension and atherosclerosis.

12 Claims, No Drawings

IMIDAZOLYL-SUBSTITUTED PHENYLACETIC ACID PROLINAMIDES

The invention relates to imidazolyl-substituted phenylacetic acid prolinamides, processes for their preparation and their use in medicaments, in particular as hypotensive and antiatherosclerotic agents.

It is known that renin, a proteolytic enzyme, eliminates the decapeptide angiotensin I from angiotensinogen in vivo, and the angiotensin I is in turn degraded in the lung, the kidneys or other tissues to give the hypertensive octapeptide angiotensin II. The various effects of angiotensin II, such as, for example, vasoconstriction, $Na^+$ retention in the kidney, aldosterone release in the adrenal gland and increase in tone of the sympathetic nervous system act synergistically in the sense of a blood pressure increase.

Moreover, angiotensin II has the property of promoting the growth and the replication of cells such as, for example, cardiac muscle cells and smooth muscle cells, these growing and proliferating in an increased manner in various disease states (for example hypertension, atherosclerosis and cardiac insufficiency).

Apart from inhibition of renin activity, a possible starting point for intervention in the renin-angiotensin system (RAS) is the inhibition of the activity of the angiotensin-converting enzyme (ACE) and the blockade of angiotensin II receptors.

The present invention relates to imidazolyl-substituted phenylacetic acid prolinamides of the general formula (I)

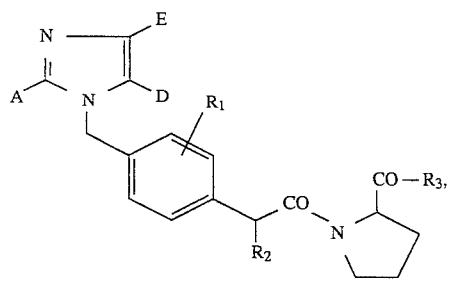

in which

A represents straight-chain or branched alkyl or alkenyl each having up to 8 carbon atoms, or represents cycloalkyl having 3 to 8 carbon atoms, E represents hydrogen, halogen or perfluoroalkyl having up to 5 carbon atoms, D represents a group of the formula $-CH_2-OR^4$ or $-CO-OR^5$,
  in which
  $R^4$ denotes hydrogen or straight-chain or branched alkyl having up to 8 carbon atoms,
  $R^5$ denotes hydrogen, hydroxyl or straight-chain or branched alkoxy having up to 8 carbon atoms, $R^1$ represents hydrogen, halogen, nitro, hydroxyl, trifluoromethyl, trifluoromethoxy, straight-chain or branched alkyl, alkoxy or alkoxycarbonyl each having up to 6 carbon atoms, cyano or carboxyl, $R^2$ represents hydrogen, straight-chain or branched alkyl having up to 8 carbon atoms, or cycloalkyl having 3 to 8 carbon atoms, $R^3$ represents hydroxyl, benzyloxy or straight-chain or branched alkoxy having up to 8 carbon atoms, or represents a group of the formula

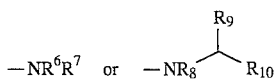

in which
$R^6$, $R^7$ and $R^8$ are identical or different and denote hydrogen or straight-chain or branched alkyl having up to 8 carbon atoms,
or
$R^6$ has the abovementioned meaning
and
$R^7$ denotes a radical of the formula $-SO_2R^{11}$,
  in which
  $R^{11}$ denotes straight-chain or branched alkyl having up to 4 carbon atoms, which is optionally substituted by phenyl or cycloalkyl having 3 to 6 carbon atoms, or denotes phenyl which is optionally substituted by straight-chain or branched alkyl having up to 4 carbon atoms,
$R^9$ denotes phenyl which is optionally substituted up to 2 times by identical or different substituents from the series consisting of halogen, nitro, hydroxyl, trifluoromethyl, trifluoromethoxy, straight-chain or branched alkyl, alkoxy or alkoxycarbonyl each having up to 6 carbon atoms, cyano, carboxyl, cycloalkyl having 3 to 6 carbon atoms and phenyl,
$R^{10}$ denotes carboxyl or straight-chain or branched alkoxycarbonyl having up to 8 carbon atoms, or denotes a radical of the formula $-CH_2OR^{12}$, $-CO-NR^{13}R^{14}$ or $-CH_2NR^{13}R^{14}$,
  in which
  $R^{12}$ denotes hydrogen, benzyl or straight-chain or branched alkyl having up to 8 carbon atoms,
  $R^{13}$ and $R^{14}$ are identical or different and denote hydrogen, phenyl or straight-chain or branched alkyl having up to 6 carbon atoms,
if appropriate in an isomeric form, and their salts.

The compounds of the general formula (I) according to the invention can also be present in the form of their salts. In general, salts with organic or inorganic bases or acids may be mentioned here.

In the context of the present invention, physiologically acceptable salts are preferred. Physiologically acceptable salts of the imidazolyl-substituted phenylacetic acid prolinamides can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, and also ammonium salts which are derived from ammonia, or organic amines such as, for example, ethyl amine, di- or triethylamine, di- or triethanolamine, dicyclohexylamine, dimnethylaminoethanol, arginine, lysine or ethylenediamine.

The compounds according to the invention can exist in stereoisomeric forms which either behave as image and mirror image (enantiomers), or which do not behave as image and mirror image (diastereomers). The invention relates both to the enantiomers or diastereomers or to their respective mixtures. Like the diastereomers, the racemic forms can be separated into the stereoisomerically uniform constituents in a known manner.

Preferred compounds of the general formula (I) are those in which

A represents straight-chain or branched alkyl or alkenyl each having up to 6 carbon atoms, or represents cyclopropyl, cyclobutyl; cyclopentyl, cyclohexyl or cycloheptyl, E represents hydrogen, fluorine, chlorine, bromine or perfluoroalkyl having up to 4 carbon atoms, D represents a group of the formula —$CH_2OR^4$ or —CO—$R^5$,
in which
$R^4$ denotes hydrogen or straight-chain or branched alkyl having up to 6 carbon atoms,
$R^5$ denotes hydrogen, hydroxyl or straight-chain or branched alkoxy having up to 6 carbon atoms, $R^1$ represents hydrogen, fluorine, chlorine, bromine, trifluoromethyl, cyano or straight-chain or branched alkyl, alkoxy or alkoxycarbonyl each having up to 5 carbon atoms, $R^2$ represents hydrogen, straight-chain or branched alkyl having up to 6 carbon atoms, cyclopentyl, cyclohexyl or cycloheptyl, $R^3$ represents hydroxyl, benzyloxy or straight-chain or branched alkoxy having up to 6 carbon atoms, or represents a group of the formula

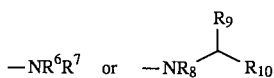

in which
$R^6$, $R^7$ and $R^8$ are identical or different and denote hydrogen or straight-chain or branched alkyl having up to 6 carbon atoms,
or
$R^6$ has the abovementioned meaning
and
$R^7$ denotes a radical of the formula —$SO_2R^{11}$,
in which
$R^{11}$ denotes straight-chain or branched alkyl having up to 3 carbon atoms, benzyl or p-tolyl,
$R^9$ denotes phenyl which is optionally substituted by fluorine, chlorine, bromine, trifluoromethyl, carboxyl or straight-chain or branched alkyl, alkoxy or alkoxycarbonyl each having up to 4 carbon atoms,
$R^{10}$ denotes carboxyl or straight-chain or branched alkoxycarbonyl having up to 6 carbon atoms, or denotes a radical of the formula —$CH_2$—$OR^{12}$, —CO—$NR^{13}R^{14}$ or —$CH_2NR^{13}R^{14}$,
in which
$R^{12}$ denotes hydrogen, benzyl or straight-chain or branched alkyl having up to 6 carbon atoms,
$R^{13}$ and $R^{14}$ are identical or different and denote hydrogen, phenyl or straight-chain or branched alkyl having up to 4 carbon atoms,
if appropriate in an isomeric form, and their salts.

Particularly preferred compounds of the general formula (I) are those
in which
A represents straight-chain or branched alkyl or alkenyl each having up to 4 carbon atoms, or represents cyclopropyl, cyclopentyl or cyclohexyl, E represents hydrogen, fluorine, chlorine or perfluoroalkyl having up to 2 carbon atoms, D represents a group of the formula —$CH_2OR^4$ or —CO—$R^5$,
in which
$R^4$ denotes hydrogen or straight-chain or branched alkyl having up to 4 carbon atoms,
$R^5$ denotes hydrogen, hydroxyl or straight-chain or branched alkoxy having up to 4 carbon atoms, $R^1$ represents hydrogen, fluorine, chlorine, bromine, trifluoromethyl, trifluoromethoxy, methyl or isobutyl, $R^2$ represents hydrogen, straight-chain or branched alkyl having up to 4 carbon atoms, cyclopentyl, cyclohexyl or cycloheptyl, $R^3$ represents hydroxyl, benzyloxy or straight-chain or branched alkoxy having up to 4 carbon atoms, or represents a group of the formula

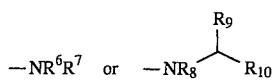

in which
$R^6$, $R^7$ and $R^8$ are identical or different and denote hydrogen or straight-chain or branched alkyl having up to 4 carbon atoms,
or
$R^6$ has the abovementioned meaning
and
$R^7$ denotes a radical of the formula —$SO_2R^{11}$
in which
$R^{11}$ denotes methyl, benzyl or p-tolyl,
$R^9$ denotes phenyl which is optionally substituted by fluorine, chlorine, bromine, trifluoromethyl, trifluoromethoxy or methyl,
$R^{10}$ denotes carboxyl or straight-chain or branched alkoxycarbonyl having up to 4 carbon atoms, or denotes a radical of the formula —$CH_2$—$OR^{12}$, —CO—$NR^{13}R^{14}$ or —$CH_2NR^{13}R^{14}$,
in which
$R^{12}$ denotes hydrogen, benzyl or straight-chain or branched alkyl having up to 4 carbon atoms,
$R^{13}$ and $R^{14}$ are identical or different and denote hydrogen or straight-chain or branched alkyl having up to 3 carbon atoms,
if appropriate in an isomeric form, and their salts.

Very particularly preferred compounds of the general formula (I) are those
in which
$R^2$ represents cyclopentyl or cycloheptyl.

A process for the preparation of the compounds of the general formula (I) according to the invention has additionally been found, characterized in that
compounds of the general formula (II)

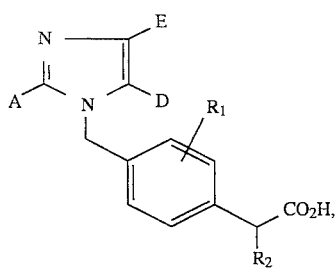

in which

A, E, D, $R^1$ and $R^2$ have the abovementioned meaning, are reacted with proline derivatives of the, general formula (III)

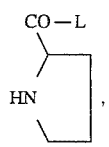

in which

L represents straight-chain or branched $(C_1-C_4)$-alkoxy or benzyloxy, in inert solvents, in the presence of a base and/or of a dehydrating agent, and in the case of the proline acids ($R^3$=OH), the esters are hydrolyzed, and in the case of the prolinamides ($R^6/R^7$=H or alkyl) starting from the acids, if appropriate after prior activation, reacted as described above with amines of the general formula (IV)

$$HNR^6R^7 \quad (IV)$$

in which $R^6$ and $R^7$ have the abovementioned meaning, and in the case of the proline phenylglycinamides ($-NR^8-CHR^9-R^{10}$) the acids are reacted, as described above, in inert solvents in the presence of a base and/or of an auxiliary with compounds of the general formula (V)

in which $R^8$, $R^9$ and $R^{10}$ have the abovementioned meaning, and if appropriate the substituents A, B, D and $R^1$ are introduced or converted into other groups by customary methods, for example by reduction, oxidation, alkylation or hydrolysis, and if appropriate the isomers are separated, and in the case of the preparation of the salts reacted with an appropriate base or acid.

The process according to the invention can be illustrated by way of example by the following reaction scheme:

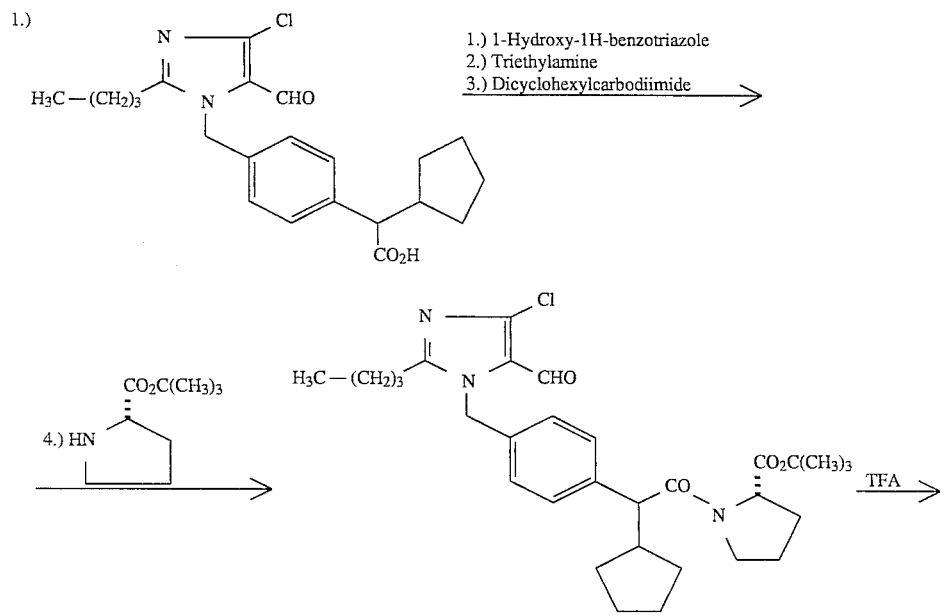

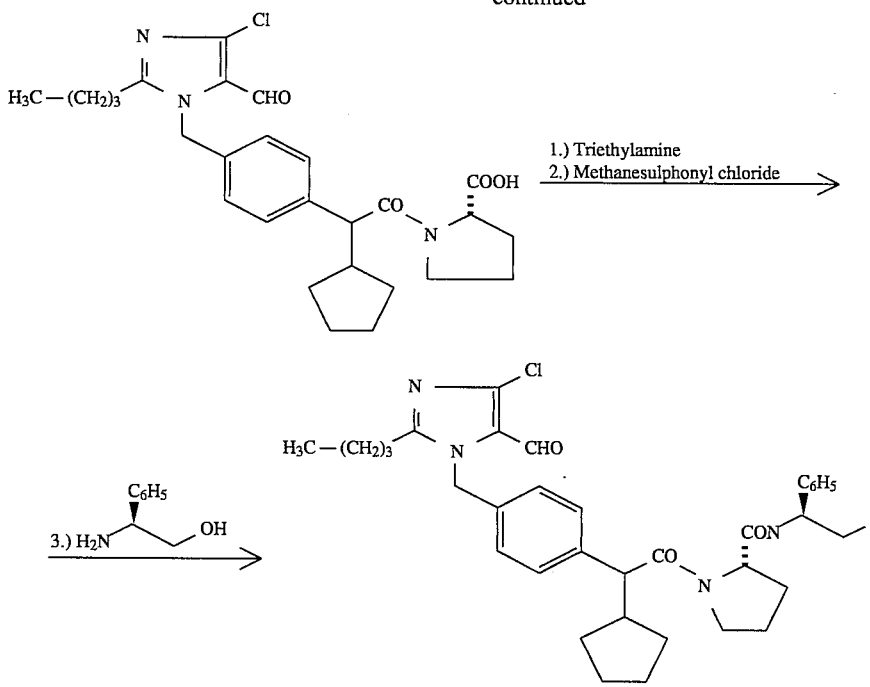

Suitable solvents for the process are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane, or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dimethylformamide and tetrahydrofuran are preferred.

The bases employed for the process according to the invention can in general be inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate, potassium carbonate or caesium carbonate, alkaline earth metal carbonates such as calcium carbonate, or alkali metal or alkaline earth metal alkoxides such as sodium methoxide or potassium methoxide, sodium ethoxide or potassium ethoxide or potassium tert-butoxide, or organic amines (trialkyl($C_1$–$C_6$)amines) such as triethylamine, or heterocycles such as 1,4-diazabicyclo-[2.2.2]octane (DABCO), 1,8-diazabicyclo[5.4.0]undec-7-ene (DBU), pyridine, diaminopyridine, methylpiperidine or morpholine. It is also possible to employ alkali metals such as sodium or their hydrides such as sodium hydride as bases. Sodium hydride, potassium carbonate, triethylamine, pyridine and potassium tert-butoxide are preferred.

In general the base is employed in an amount from 0.05 to 10 mol, preferably from 1 mol to 2 mol, relative to 1 mol of the compound of the formula (III).

The process according to the invention is in general carried out in a temperature range from –30° C. to +100° C., preferably from –10° C. to +60° C.

The process according to the invention is in general carried out at normal pressure. However, it is also possible to carry out the process at elevated pressure or at reduced pressure (for example in a range from 0.5 to 5 bar).

Suitable bases for the hydrolysis are the customary inorganic bases. These preferably include alkali metal hydroxides or alkaline earth metal hydroxides such as, for example, lithium hydroxide, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert-butoxide. Lithium hydroxide, sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is preferably carried out using acids such as, for example, trifluoroacetic acid, acetic acid, hydrochloric acid, hydrochloric acid/dioxane, hydrobromic acid, methanesulphonic acid, sulphuric acid or perchloric acid, particularly preferably using trifluoroacetic acid or hydrochloric acid/dioxane.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

When carrying out the reaction, the carboxylates of the compounds according to the invention are formed in the first step as intermediates which can be isolated. The acids according to the invention are obtained by treating the carboxylates with customary inorganic acids. These preferably include acids such as, for example, hydrochloric acid, hydrobromic acid, sulphuric acid, phosphoric acid or trifluoroacetic acid. It has also proven advantageous in this case in the preparation of the carboxylic acids to acidify the basic reaction mixture from the hydrolysis in a second step without isolation of the carboxylates. The acids can then be isolated in a customary manner.

The amidation and the sulphoamidation is in general carried out in one of the abovementioned solvents, preferably in tetrahydrofuran or dichloromethane.

The amidation or sulphoamidation can proceed from the appropriate acids, if appropriate via the activated stage of the acid halides or mixed anhydrides, which can be prepared from the corresponding acids by reaction with thionyl chloride, phosphorus trichloride, phosphorus pentachloride, phosphorus tribromide or oxalyl chloride or methanesulphonyl chloride.

The amidation or sulphoamidation is in general carried out in a temperature range from −50° C. to +80° C., preferably from −30° C. to +20° C., and at normal pressure.

In addition to the abovementioned bases, suitable bases for this reaction are preferably triethylamine and/or dimethylaminopyridine, DBU or DABCO.

The base is employed in an amount from 0.5 mol to 10 mol, preferably from 1 mol to 5 mol, relative to 1 mol of the compounds of the general formula (V).

Acid-binding agents which can be employed for the amidation or sulphoamidation are alkali metal or alkaline earth metal carbonates such as sodium carbonate, potassium carbonate, alkali metal or alkaline earth metal hydroxides such as, for example, sodium hydroxide or potassium hydroxide, or organic bases such as pyridine, triethylamine, N-methylpiperidine, or bicyclic amidines such as 1,5-diazabicyclo[3.4.0]non-5-ene (DBN) or 1,5-diazabicyclo[3.4.0]undec-5-ene (DBU). Triethylamine is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazoliumcompounds such as 2-ethyl-5-phenyl-1,2-oxazolium-3-sulphonate or propanephosphonic anhydride or isobutyl chloroformate, or benzotriazolyl-oxy-tris-(dimethylamino)phosphonium hexafluorophosphate or diphenyl phosphoramidate or methanesulphonyl chloride, if appropriate in the presence of bases such as triethylamine or N-ethylmorpholino or N-methylpiperidine or dicyclohexylcarbodiimide and N-hydroxysuccinimide.

The acid-binding agents and dehydrating reagents are in general employed in an amount from 0.5 to 3 mol, preferably from 1 to 1.5 mol, relative to 1 mol of the corresponding carboxylic acids.

The abovementioned derivatization of the substituents A, E, D and $R^1$ is in general carried out by methods known from the literature, where the reduction of aldehydes or alkoxycarbonyl compounds to alcohols (a), the reduction of double bonds (b) and the alkylation (c) will be illustrated by way of example by the following:

a) The reduction of carbonyl compounds to the corresponding alcohols is in general carried out using hydrides, such as lithium aluminium hydride or sodium borohydride, preferably in the case of alkoxycarbonyl compounds using lithium aluminium hydride and in the case of aldehydes preferably using sodium borohydride in inert solvents such as ethers, hydrocarbons or alcohols or mixtures thereof, preferably in ethers such as, for example, diethyl ether, tetrahydrofuran or dioxane, or alcohols such as ethanol, in the case of the aldehydes preferably using sodium borohydride in ethanol, in a temperature range from 0° C. to +150° C., preferably from +20° C. to +100° C., at normal pressure.

The reduction of a double bond is in general carried out by hydrogenation with hydrogen in the presence of a catalyst such as, for example, platinum or platinum oxides, rhodium, ruthenium, chlorotris(triphenylphosphine)rhodium, or palladium on animal charcoal, preferably using palladium on animal charcoal in a temperature range from 0° C. to +150° C., preferably from +25° C. to +100° C.

b) Suitable solvents for the hydrogenation are protic solvents such as, for example, methanol, ethanol and/or aprotic solvents such as, for example, tetrahydrofuran, toluene, dimethylformamide, methylene chloride, dioxane or ethyl acetate.

The hydrogenation is carried out at pressure from 1 to 300 atm, preferably at 1 to 20 atm.

c) The alkylation is in general carried out in one of the abovementioned solvents using alkylating agents such as, for example, $(C_1–C_8)$-alkyl halides, sulphonic acid esters or substituted or unsubstituted $(C_1–C_6)$-dialkyl or $(C_1–C_{10})$-diaryl sulphates, preferably methyl iodide, p-toluenesulphonic esters or dimethyl sulphate.

The compounds of the general formula (II) are in some cases new and can be prepared, for example, by reacting compounds of the general formula (VI)

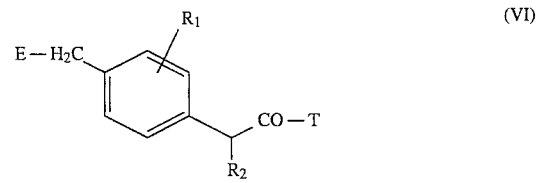

(VI)

in which $R^1$ and $R^2$ have the abovementioned meaning,

E represents a typical leaving group such as, for example, chlorine, bromine, iodine, rosylate or mesylate, preferably bromine, and T represents straight-chain or branched $(C_1–C_4)$-alkoxy, with imidazoles of the general formula (VII)

(VII)

in which

A, B and D have the abovementioned meaning, in one of the abovementioned solvents, preferably dimethylformamide, and in the presence of one of the abovementioned bases, preferably sodium hydride or potassium carbonate, if appropriate under a protective gas atmosphere, and in the case of the acids the esters are hydrolyzed as described above.

In general, the base is employed in an amount from 0.05 mol to 10 mol, preferably from 1 mol to 2 mol, relative to 1 mol of the compound of the formula (VII).

The process is in general carried out in a temperature range from −30° C. to +100° C., preferably from −10° C. to +10° C.

The process is in general carried out at normal pressure. However, it is also possible to carry out the process at elevated pressure or at reduced pressure (for example in a range from 0.5 to 5 bar).

The compounds of the general formulae (III), (IV), (V), (VI) and (VII) are in the main known or can be prepared by customary methods.

The compounds of the general formula (I) according to the invention exhibit an unforeseeable, useful spectrum of pharmacological action.

The compounds according to the invention have a specific A II-antagonistic action, since they competitively inhibit the binding of angiotensin II to the receptors. They suppress the vasoconstrictory and aldosterone secretion-stimulating effects of angiotensin II. They moreover inhibit the proliferation of smooth muscle cells.

They can therefore be employed in medicaments for the treatment of arterial hypertension and atherosclerosis. They can moreover be employed for the treatment of coronary heart diseases, cardiac insufficiency, disorders of the brain function, ischemic cerebral diseases, peripheral circulatory disorders, functional disorders of the kidney and adrenal gland, bronchospastic diseases and respiratory tract diseases having a vascular component, sodium retention and oedemas.

Investigation of the Inhibition of the Contraction Induced by Agonists

Rabbits of either sex are stunned by a blow to the back of the head and bled out, or in some cases anaesthetized with Nembutal (about 60–80 mg/kg i.v.) and sacrificed by opening the thorax. The thorax aorta is removed, freed from adhering connective tissue, divided into ring segments 1.5 mm wide and individually transferred under an initial loading of about 3.5 g to 10 ml organ baths containing Krebs-Henseleit nutrient solution, which is temperature-controlled at 37° C. and aerated with 95% $O_2$/5% $CO_2$, of the following composition: 119 mmol/l of NaCl; 2.5 mmol/l of $CaCl_2 \times 2H_2O$; 1.2 mmol/l of $KH_2PO_4$; 10 mmol/l of glucose; 4.8 mmol/l of KCl; 1.4 mmol/l of $MgSO_4 \times 7H_2O$ and 25 mmol/l of $NaHCO_3$.

The contractions are detected isometrically by Statham UC2 cells by means of bridge amplifiers (ifd Mülheim or DSM Aalen) and digitalized and assessed by means of A/D converters (System 570, Keithley Munich). Agonist dose response curves (DRC) are carried out hourly. With each DRC, 3 or 4 individual concentrations are applied to the baths at a 4 min interval. After the end of the DRC and subsequent washing-out cycles (16 times in each case about 5 sec/min with the abovementioned nutrient solution), a 28-minute rest or incubation phase follows, during which the contractions as a rule reach the starting value again.

The height of the 3rd DRC, in a normal case, is used as a reference variable for the assessment of the test substance to be investigated in further runs, which is applied to the baths in the following DRCs in increasing doses in each case at the start of the incubation period. Each aorta ring is in this case stimulated for the whole day, always with the same agonist.

Agonists and Their Standard Concentrations
(Application Volume per Individual Dose=100 μl)

| | | |
|---|---|---|
| KCl | 22.7; 32.7; 42.7; 52.7 | mmol/l |
| 1-Noradrenaline | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$ | g/ml |
| Methoxamine | $10^{-7}$; $10^{-6}$; $10^{-5}$ | g/ml |
| Angiotensin II | $3 \times 10^{-9}$; $10^{-8}$; $3 \times 10^{-8}$; $10^{-7}$ | g/ml |

For the calculation of the $IC_{50}$ (concentration at which the substance to be investigated causes a 50% inhibition), the effect is in each case based on the 3rd= submaximal agonist concentration.

The compounds according to the invention inhibit the contraction of the isolated rabbit aorta induced by angiotensin II in a dose-dependent manner. The contraction induced by potassium depolarization or other agonists was not inhibited or only weakly inhibited at high concentrations.

Blood Pressure Measurements on the Angiotensin II-Infused Rat

Male Wistar rats (Moellegaard, Copenhagen, Denmark) having a body weight of 300–350 g are anaesthetized with thiopental (100 mg/kg i.p.). After tracheotomy, a catheter for blood pressure measurement is inserted in the femoral artery and a catheter for angiotensin II infusion and a catheter for substance administration are inserted in the femoral veins. After administration of the ganglionic blocker pentolinium (5 mg/kg i.v.), the angiotensin II infusion (0.3 μg/kg/min) is started. As soon as the blood pressure values have reached a stable plateau, the test substances are either administered intravenously or orally as a suspension or solution in 0.5% Tylose.

Determination of the Antihypertensive Activity in Conscious Hypertensive Rats

The oral antihypertensive activity of the compounds according to the invention was tested in conscious rats using surgically induced unilateral renal artery stenosis. To do this, the right renal artery was constricted with a silver clip of 0.18 mm internal width. In this form of hypertension, the plasma renin activity is increased in the first six weeks after intervention.

The arterial blood pressure of these animals was measured in a blood-free manner at defined time intervals after substance administration using the "tail cuff". The substances to be tested were suspended in a Tylose suspension and administered intragastrally ("orally") in various doses by stomach tube. The compounds according to the invention reduce the arterial blood pressure of the hypertensive rats at a clinically relevant dose.

Additionally, the compounds according to the invention inhibit the specific binding of radioactive angiotensin II in a concentration-dependent manner.

Interaction of the Compounds According to the Invention with the Angiotensin II Receptor in Membrane Fractions of the Adrenal Gland Cortex (Bovine)

Bovine adrenal gland cortices (AGC), which have been freshly removed and carefully freed from gland medulla, are comminuted in sucrose solution (0.32M) with the aid of an Ultra-Turrax (Janke & Kunkel, Staufen i.B.) to give a coarse membrane homogenate and partially purified in two centrifugation steps to give membrane fractions. The receptor binding investigations are carried out on partially purified membrane fractions of bovine AGC using radioactive angiotensin II in an assay volume of 0.25 ml, which specifically contains the partially purified membranes (50–80 μg), $^3$H-angiotensin II (3–5 nM), test buffer solution (50 mM Tris, pH 7.2), 5 mM $MgCl_2$ and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM Tris/HCl, pH 7.4, 5% PEG 6000). The analysis of the raw data was carried out using computer programs to give $K_i$ or $IC_{50}$ values ($K_i$: $IC_{50}$ values corrected for the radioactivity used; $IC_{50}$ values: concentration at which the substance to be investigated causes a 50% inhibition of the specific binding of the radioligand).

TABLE A

| Ex. No. | $IC_{50}$ [nM] |
|---|---|
| 7 | 580 |
| 12 | 290 |

Investigation of the Inhibition of the Proliferation of Smooth Muscle Cells by the Compounds According to the Invention To determine the antiprofilerative action of the compounds, smooth muscle cells are used which are obtained from aortas of rats by the media explant technique [R. Ross, J. Cell. Biol. 50, 172, 1971]. The cells are inoculated in suitable culture dishes, as a rule 96-hole plates, and cultured in 5% $CO_2$ at 37° C. for 2–3 days in medium 199 containing 7.5% FCS and 7.5% NCS, 2 mM L-glutamine and 15 mM HEPES, pH 7.4. The cells are then synchronized by withdrawal of serum for 2–3 days and then stimulated into growth with serum or other factors. Test compounds are simultaneously added. After 16–20 hours, 1 μCi $^3$H-thymidine is added and after a further 4 hours the incorporation of this substance into the TCA-precipitatable DNA of the cells is determined. To determine the $IC_{50}$ values, the active compound concentration is determined which, on sequential dilution of the active compound, causes semi-maximal inhibition of the thymidine incorporation produced by 10% FCS.

TABLE B

| Ex. No. | $IC_{50}$ [nM] |
|---|---|
| 9 | 860 |
| 14 | 450 |

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proven advantageous in the case of intravenous administration to administer amounts of about 0.001 to 1 mg/kg, preferably about 0.01 to 0.5 mg/kg, of body weight to achieve effective results, and in the case of oral administration the dose is about 0.01 to 20 mg/kg, preferably 0.1 to 10 mg/kg, of body weight.

In spite of this, it may sometimes be necessary to deviate from the amounts mentioned, namely depending on the body weight or the type of application route, on individual behaviour towards the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual doses over the course of the day.

Eluents (A) Dichloromethane/methanol/ammonia=9:1:0.1
(B) Ethyl acetate/petroleum ether=7:3
(C) Ethyl acetate/petroleum ether=3:7
(D) Dichloromethane/methanol=9:1
(E) Dichloromethane/methanol/acetic acid=9:1:0.1

STARTING COMPOUNDS

Example I tert-Butyl 4-methylphenylacetate

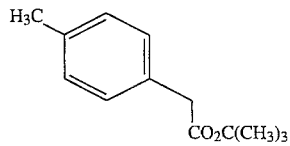

450 g (3 mol) of 4-methylphenylacetic acid, 1.13 l (12 mol) of tert-butanol and 90 g (0.74 mol) of dimethylaminopyridine are dissolved in 2 l of dichloromethane. After addition of 680 g (3.3 mol) of dicyclohexylcarbodiimide, dissolved in 400 ml of dichloromethane, the mixture is stirred at 25° C. for 20 h, the precipitated urea is filtered off with suction and washed with 200 ml of dichloromethane, and the organic phase is washed twice each with 500 ml of 2N hydrochloric acid and water. The organic phase is concentrated and distilled.

Yield: 408 g (66% of theory) Boiling point: 73°–78° C./0.2 mm

Example II tert-Butyl 2-cyclopentyl-2-(4-methylphenyl)acetate

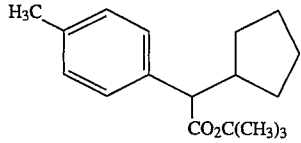

33.5 g (0.3 mol) of potassium tert-butoxide are initially introduced at 0° C. into 100 ml of DMF with exclusion of moisture, and 51.6 g (0.25 mol) of tert-butyl 4-methylphenylacetate in 250 ml of DMF are added dropwise. The mixture is stirred at 0° C. for 30 min and 32.2 ml (0.3 mol) of cyclopentyl bromide in 150 ml of DMF are added dropwise at 5°–15° C. and the mixture is stirred at 25° C. for 20 h. After concentration, the residue is partitioned between water/diethyl ether, and the ether phase is dried over sodium sulphate and concentrated. The product crystallizes out.

Yield: 67 g (97.5% of theory) Solidification point: 51°–53° C.

Example III tert-Butyl 2-(4-bromomethyl-phenyl)-2-cyclopentyl-acetate

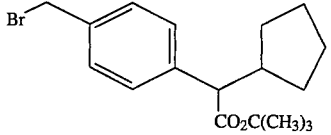

27.4 g (0.1 mol) of tert-butyl 2-cyclopentyl-2-(4-methylphenyl)-acetate are dissolved in 200 ml of carbon tetrachloride and the mixture is heated to boiling. After addition of 0.82 g of azobisisobutyronitrile, 18.7 g (0.105 mol) of N-bromosuccinimide are added in portions and the mixture is then refluxed for 1 h, cooled to 0° C. and the succinimide is filtered off. After concentration of the filtrate, the product precipitates. It is washed with petroleum ether (40/60) and dried.

Yield: 20 g (57% of theory) Solidification point: 73°–76° C.

Example IV tert-Butyl 2-[4-(2-butyl-4-chloro-5-formyl-imidazol-1-yl-methyl)phenyl]-2-cyclopentyl-acetate

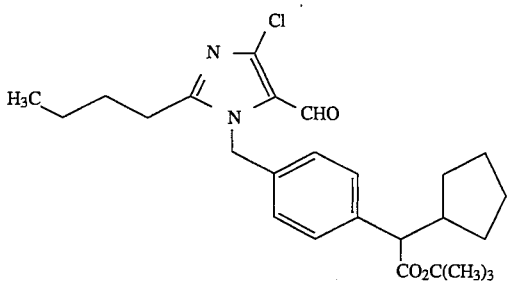

1.6 g (0.053 mol) of sodium hydride (80% strength) are suspended in 50 ml of DMF under protective gas, 10 g (0.053 mol) of 2-butyl-5-formyl-4-chloroimidazole (preparation according to EP 324 377) are added dropwise at 0° C. in 100 ml of DMF, then the mixture is stirred for 15 min at 0° C. and 18.9 g (0.053 mol) of tert-butyl 2-(4-bromomethylphenyl)-2-cyclopentylacetate in 100 ml of DMF are added dropwise. The mixture is additionally stirred at 0° C. for 2 h, the solvent is evaporated, the residue is taken up in diethyl ether, the solid is filtered off and, after concentration, the residue is chromatographed on silica gel 60 using dichloromethane.

Yield: 16.2 g (66.7% of theory) Solidification point: 101°–102° C.

Example V

2-[4-(2-Butyl-4-chloro-5-formyl-imidazol-1-yl-methyl)-phenyl]-2-cyclopentylacetic acid

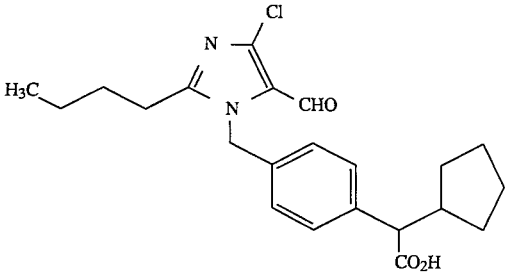

2.3 g (5 mmol) of the compound from Example IV are stirred at 25° C. for 5 h in 5 ml of dichloromethane and 5 ml of trifluoroacetic acid. After concentration, the crude product is chromatographed on silica gel 60 using dichloromethane/methanol (100:5).

Yield: 1.8 g (87.6% of theory) Solidification point: 95°–98° C.

PREPARATION EXAMPLES

Example 1 and Example 2

2-[4-(2-Butyl-4-chloro-5-formyl-imidazol-1-yl-methyl)phenyl]-2-cyclopentylacetic acid L-(proline tert-butyl ester) amide

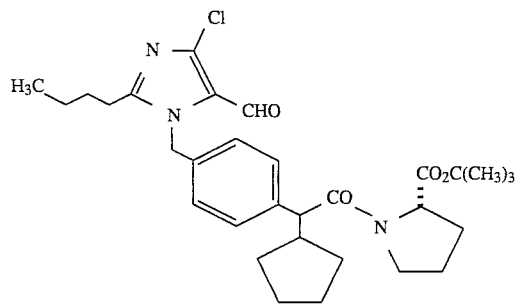

1.0 g (2.5 mmol) of the compound from Example V is treated at room temperature with 0.4 g (2.7 mmol) of 1-hydroxy-1H-benzotriazole in 30 ml of dichloromethane, the mixture is cooled to 0° C., and 0.51 g (5 mmol) of triethylamine and a solution of 0.56 g (2.7 mmol) of dicyclohexylcarbodiimide in 10 ml of dichloromethane are then added dropwise. After 30 minutes, a solution of 0.51 g (3.0 mmol) of L-proline tert-butyl ester in 10 ml of dichloromethane is added at 0° C. and the mixture is stirred overnight at room temperature. For working up, it is treated with water and dichloromethane, shaken and separated, the aqueous phase is extracted a further two times with dichloromethane, and the combined organic phases are dried over sodium sulphate, filtered and concentrated and the residue is chromatographed on silica gel 60 (ethyl acetate / petroleum ether=1:1).

Total yield: 1.14 g (2.0 mmol) of diastereomer A and diastereomer B: 82% of theory $R_f$ 0.84 (diastereomer A) (Example 1) (ethyl acetate/petroleum ether=7:3)

0.79 (diastereomer B) (Example 2) (ethyl acetate/petroleum ether=7:3)

The compound shown in Table 1 is prepared in analogy to the procedure of Examples 1 and 2:

TABLE 1

| Ex. No. | D | $R^3$ | $R_f$ (LM) | * |
|---|---|---|---|---|
| 3 | —CHO | —O—CH$_2$—C$_6$H$_5$ | 0.26 (C) | rac |

Example 4

2-[4-(2-Butyl-4-chloro-5-formyl-imidazol-1-yl-methyl)-phenyl]-2-cyclopentylacetic acid L-prolinamide

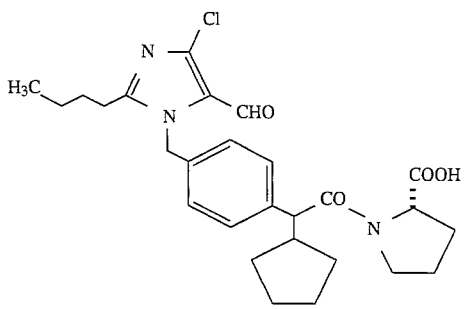

In analogy to the procedure of Example V, the title compound is prepared by ester cleavage of 0.6 g (1.1 mmol) of the compound from Example 1.

Yield: 0.48 g (1 mmol) 98% of theory $R_f$=0.53 (dichloromethane/methanol 9:1)

Example 5

2-[4-(2-Butyl-4-chloro-5-formyl-imidazol-1-yl-methyl)-phenyl]-2-cyclopentylacetic acid (L-prolinamido) amide

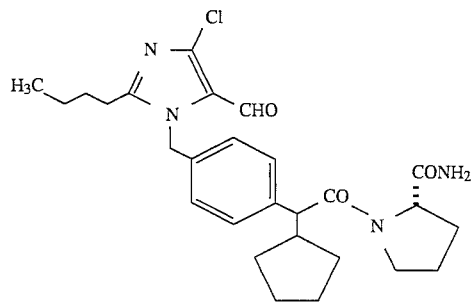

The title compound is prepared in analogy to the procedure of Examples 1 and 2 from 1.0 g (2.5 mmol) of the compound from Example V and 0.34 g (3.0 mmol) of L-prolinamide.

Yield: 0.91 g (1.8 mmol) 73% of theory $R_f$=0.65 (dichloromethane/methanol/ammonia=9:1:0.1)

Example 6

2-[4-(2-Butyl-4-chloro-5-carboxy-imidazol-1-yl-methyl)phenyl]-2-cyclopentylacetic acid L-prolinamide

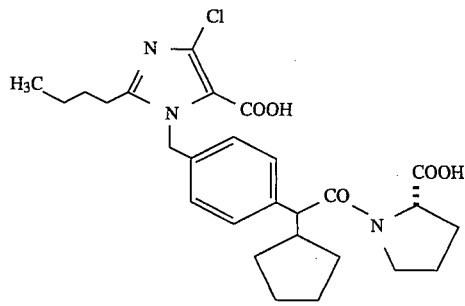

0.2 g (0.4 mmol) of the compound from Example 4 is treated at room temperature with 2.4 ml of 1M potassium permanganate solution in a mixture of 3 ml of tert-butanol and 1.6 ml of 1.25M sodium dihydrogen phosphate solution (pH 7) and the mixture is stirred for 10 minutes. After addition of 5 ml of saturated sodium sulphite solution (ice-cooling), it is acidified with 1N HCl and extracted three times with ethyl acetate. The combined organic phases are dried over sodium sulphate, filtered and concentrated, and the residue is chromatographed on silica gel 60 (dichloromethane/methanol= 9:1).

Yield: 0.06 g (0.12 mmol) 30.6% of theory $R_f$=0.35 (dichloromethane/methanol/acetic acid= 9:1:0.1)

Example 7

2-[4-(2-Butyl-4-chloro-5-carboxy-imidazol-1-yl-methyl)-phenyl]-2-cyclopentylacetic acid (L-prolinamido) amide

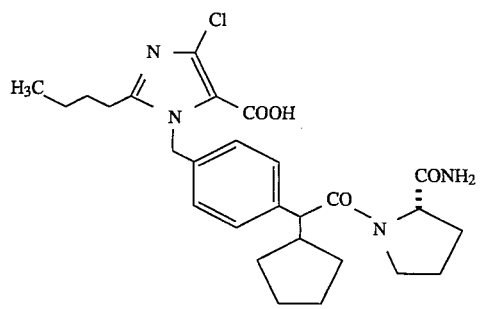

In analogy to the procedure of Example 6, the title compound is prepared from 0.3 g (0.6 mmol) of the compound from Example 5.

Yield: 0.29 g (0.57 mmol) 94% of theory $R_f$=0.31 (dichloromethane/methanol/glacial acetic acid= 9:1:0.1)

Example 8

2-[4-(2-Butyl-4-chloro-5-formyl-imidazol-1-yl-methyl)-phenyl]-2-cyclopentylacetic acid (L-proline-phenylglycinolamido) amide

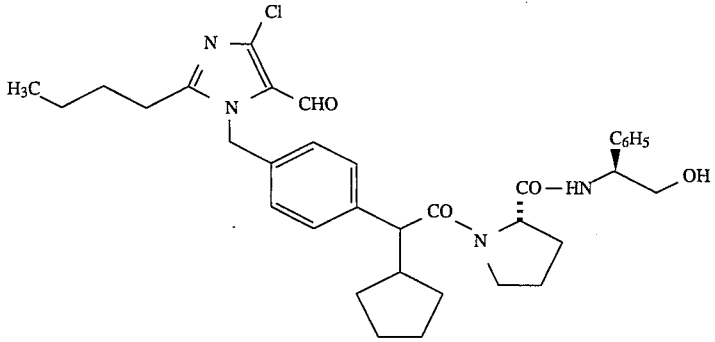

0.11 g (0.22 mmol) of the compound from Example 4 is treated at room temperature with 0.05 ml (0.44 mmol) of triethylamine in 5 ml of tetrahydrofuran, and the mixture is cooled to −30° C. with stirring. 0.03 g (0.24 mmol) of methanesulphonyl chloride is added and, after stirring for 90 minutes, a solution of 0.03 g (0.24 mmol) of L-phenylglycinol in 5 ml of tetrahydrofuran is added dropwise, and the mixture is stirred for 1 further hour at −30° C. and allowed to warm to room temperature overnight. For working up, it is treated with 5 ml of 1N acetic acid, ethyl acetate and water are added, the mixture is shaken and the aqueous phase is extracted a further two times with ethyl acetate. The combined organic phases are dried over sodium sulphate, filtered and concentrated, and the residue is chromatographed on silica gel 60 (dichloromethane/methanol=98:2).

Yield: 40.3 mg (0.065 mmol) 29.5% of theory $R_f$=0.21 (ethyl acetate/petroleum ether=7:3)

Example 9

2-[4-(2-Butyl-4-chloro-5-hydroxymethyl-imidazol-1-yl-methyl)phenyl]-2-cyclopentylacetic acid (L-prolinephenylglycinolamido) amide

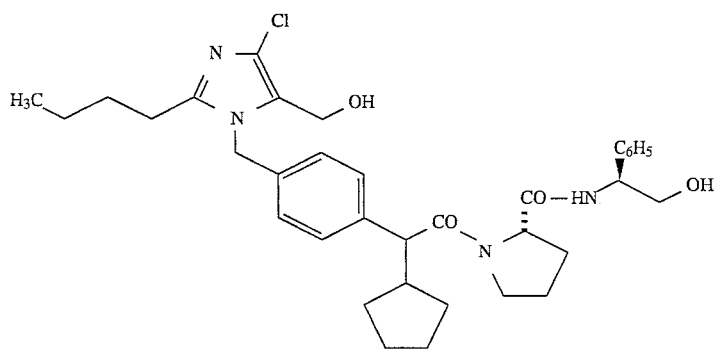

0.04 g (0.06 mmol) of the compound from Example 7 are dissolved in 2 ml of ethanol, treated with 2 mg (0.06 mmol) of sodium borohydride and the mixture is stirred at room temperature for 2 hours. For working up, it is treated with water, acidified with 1N acetic acid, extracted three times with ethyl acetate, and the combined organic phases are dried over magnesium sulphate, filtered and concentrated.

Yield: 0.03 g (0.05 mmol) 89% of theory $R_f$=0.52 (dichloromethane : methanol=9:1)

The compounds shown in Table 2 are prepared in analogy to the procedures of Examples 6, 8 and 9:

TABLE 2

| Ex. No. | D | $R^3$ | | | | |
|---|---|---|---|---|---|---|
| 10 | —CH$_2$OH | —NH$_2$ | rac | 0.38 | (D) | 9 |
| 11 | —CH$_2$OH | —O—CH$_2$—C$_6$H$_5$ | rac | 0.52 | (D) | 9 |
| 12 | —CO$_2$H | —O—CH$_2$—C$_6$H$_5$ | rac | 0.32 | (E) | 6 |
| 13 | —CH$_2$OH | —O—C(CH$_3$)$_3$ | Enant. A | 0.43 | (D) | 9 |
| 14 | —CH$_2$OH | —O—C(CH$_3$)$_3$ | Enant. B | 0.42 | (D) | 9 |
| 15 | —CHO | —NH—CH(C$_6$H$_5$)CONH$_2$ | rac | 0.56 | (D) | 8 |
| 16 | —CH$_2$OH | —NH—CH(C$_6$H$_5$)CONH$_2$ | rac | 0.55 | (D) | 9 |

We claim:

1. An imidazolyl-substituted phenylacetic acid prolinamide of the formula

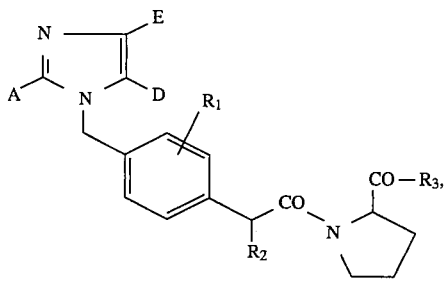

in which

A represents straight-chain or branched alkyl or alkenyl each having up to 8 carbon atoms, or represents cycloalkyl having 3 to 8 carbon atoms, E represents hydrogen, halogen or perfluoroalkyl having up to 5 carbon atoms, D represents a group of the formula —CH$_2$—OR$^4$ or —CO—OR$^5$, in which R$^4$ denotes hydrogen or straight-chain or branched alkyl having up to 8 carbon atoms, R$^5$ denotes hydrogen, hydroxyl or straight-chain or branched alkoxy having up to 8 carbon atoms, R$^1$ represents hydrogen, halogen, nitro, hydroxyl, trifluoromethyl, trifluoromethoxy, straight-chain or branched alkyl, alkoxy or alkoxycarbonyl each having up to 6 carbon atoms, cyano or carboxyl, R$^2$ represents hydrogen, straight-chain or branched alkyl having up to 8 carbon atoms, or cycloalkyl having 3 to 8 carbon atoms, R$^3$ represents hydroxyl, benzyloxy or straight-chain or branched alkoxy having up to 8 carbon atoms, or represents a group of the formula

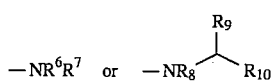

in which

R$^6$, R$^7$ and R$^8$ are identical or different and denote hydrogen or straight-chain or branched alkyl having up to 8 carbon atoms, or R$^6$ has the abovementioned meaning
and
R$^7$ denotes a radical of the formula —SO$_2$R$^{11}$, in which R$^{11}$ denotes straight-chain or branched alkyl having up to 4 carbon atoms, which is optionally substituted by phenyl or cycloalkyl having 3 to 6 carbon atoms, or denotes phenyl which is optionally substituted by straight-chain or branched alkyl having up to 4 carbon atoms, R$^9$ denotes phenyl which is optionally substituted up to 2 times by identical or different substituents from the group consisting of halogen, nitro, hydroxyl, trifluoromethyl, trifluoromethoxy, straight-chain or branched alkyl, alkoxy or alkoxycarbonyl each having up to 6 carbon atoms, cyano, carboxyl, cycloalkyl having 3 to 6 carbon atoms and phenyl, R$^{10}$ denotes carboxyl or straight-chain or branched alkoxycarbonyl having up to 8 carbon atoms, or denotes a radical of the formula —CH$_2$OR$^{12}$, —CO—NR$^{13}$R$^{14}$ or —CH$_2$NR$^{13}$R$^{14}$, in which R$^{12}$ denotes hydrogen, benzyl or straight-chain or branched alkyl having up to 8 carbon atoms, R$^{13}$ and R$^{14}$ are identical or different and denote hydrogen, phenyl or straight-chain or branched alkyl having up to 6 carbon atoms, if appropriate in an isomeric form, or a salt thereof.

2. An imidazolyl-substituted phenylacetic acid prolinamide of the formula (I) according to claim 1, in which A represents straight-chain or branched alkyl or alkenyl each having up to 6 carbon atoms, or represents cyclopropyl, cyclobutyl, cyclopentyl, cyclohexyl or cycloheptyl, E represents hydrogen, fluorine, chlorine, bromine or perfluoroalkyl having up to 4 carbon atoms, D represents a group of the formula —CH$_2$OR$^4$ or —CO—R$^5$, in which R$^4$ denotes hydrogen or straight-chain or branched alkyl having up to 6 carbon atoms, R$^5$ denotes hydrogen, hydroxyl or straight-chain or branched alkoxy having up to 6 carbon atoms, R$^1$ represents hydrogen, fluorine, chlorine, bromine, trifluoromethyl, cyano or straight-chain or branched alkyl, alkoxy or alkoxycarbonyl each having up to 5 carbon atoms, R$^2$ represents hydrogen, straight-chain or branched alkyl having up to 6 carbon atoms, cyclopentyl, cyclohexyl or cycloheptyl, R$^3$ represents hydroxyl, benzyloxy or straight-chain or branched alkoxy having up to 6 carbon atoms, or represents a group of the formula

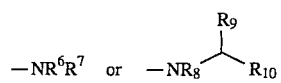

in which

R$^6$, R$^7$ and R$^8$ are identical or different and denote hydrogen or straight-chain or branched alkyl having up to 6 carbon atoms, or R$^6$ has the abovementioned meaning
and
R$^7$ denotes a radical of the formula —SO$_2$R$^{11}$, in which R$^{11}$ denotes straight-chain or branched alkyl having up to 3 carbon atoms, benzyl or p-tolyl, R$^9$ denotes phenyl which is optionally substituted by fluorine, chlorine, bromine, trifluoromethyl, carboxyl or straight-chain or branched alkyl, alkoxy or alkoxycarbonyl each having up to 4 carbon atoms, R$^{10}$ denotes carboxyl or straight-chain or branched alkoxycarbonyl having up to 6 carbon atoms, or denotes a radical of the formula —CH$_2$—OR$^{12}$, —CO—NR$^{13}$R$^{14}$ or —CH$_2$NR$^{13}$R$^{14}$, in which R$^{12}$ denotes hydrogen, benzyl or straight-chain or branched alkyl having up to 6 carbon atoms, R$^{13}$ and R$^{14}$ are identical or different and denote hydrogen, phenyl or straight-chain or branched alkyl having up to 4 carbon atoms, if appropriate in an isomeric form, or a salt thereof.

3. An imidazolyl-substituted phenylacetic acid prolinamide of the formula (I) according to claim 1, in which A represents straight-chain or branched alkyl or alkenyl each having up to 4 carbon atoms, or represents cyclopropyl, cyclopentyl or cyclohexyl, E represents hydrogen, fluorine, chlorine or perfluoroalkyl having up to 2 carbon atoms, D represents a group of the formula —CH$_2$OR$^4$ or —CO—R$^5$, in which R$^4$ denotes hydrogen or straight-chain or branched alkyl having up to 4 carbon atoms, R$^5$ denotes hydrogen, hydroxyl or straight-chain or branched alkoxy having up to 4 carbon atoms, R$^1$ represents hydrogen, fluorine, chlorine, bromine, trifluoromethyl, trifluoromethoxy, methyl or isobutyl, R$^2$ represents hydrogen, straight-chain or branched alkyl having up to 4 carbon atoms, cyclopentyl, cyclohexyl or cycloheptyl, R$^3$ represents hydroxyl, benzyloxy or straight-chain or branched alkoxy having up to 4 carbon atoms, or represents a group of the formula

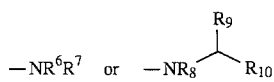

in which

R$^6$, R$^7$ and R$^8$ are identical or different and denote hydrogen or straight-chain or branched alkyl having up to 4 carbon atoms, or R$^6$ has the abovementioned meaning and R$^7$ denotes a radical of the formula —SO$_2$R$^{11}$ in which R$^{11}$ denotes methyl, benzyl or p-tolyl, R$^9$ denotes phenyl which is optionally substituted by fluorine, chlorine, bromine, trifluoromethyl, trifluoromethoxy or methyl, R$^{10}$ denotes carboxyl or straight-chain or branched alkoxycarbonyl having up to 4 carbon atoms, or denotes a radical of the formula —CH$_2$—OR$^{12}$, —CO—NR$^{13}$R$^{14}$ or —CH$_2$NR$^{13}$R$^{14}$, in which R$^{12}$ denotes hydrogen, benzyl or straight-chain or branched alkyl having up to 4 carbon atoms, R$^{13}$ and R$^{14}$ are identical or different and denote hydrogen or straight-chain or branched alkyl having up to 3 carbon atoms, if appropriate in an isomeric form, or a salt thereof.

4. An imidazolyl-substituted phenylacetic acid prolinamide according to claim 1, in which R$^2$ represents cyclopentyl or cycloheptyl.

5. An imidazolyl-substituted phenyl acetic acid prolinamide according to claim 1 wherein such compound is 2-[4-(2-Butyl-4 -chloro-5-formyl-imidazol-1-yl-methyl)-phenyl]-2-cyclopentylacetic acid L-(proline tert-butyl ester) amide of the formula

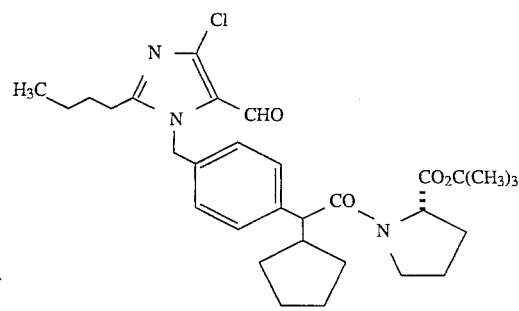

or an isomer or salt thereof.

6. An imidazolyl-substituted phenyl acetic acid prolinamide according to claim 1 wherein such compound is 2-[4-(2-Butyl-4 -chloro-5-formyl-imidazol-1-yl-methyl)-phenyl]-2-cyclopentylacetic acid L-prolinamide of the formula

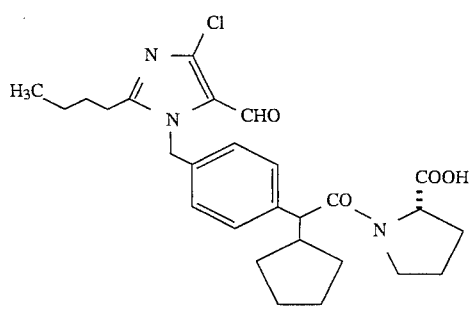

or an isomer or salt thereof.

7. An imidazolyl-substituted phenyl acetic acid prolinamide according to claim 1 wherein such compound is 2-[4-(2-Butyl-4 -chloro-5-formyl-imidazol-1-yl-methyl)-phenyl]-2-cyclopentylacetic acid (L-prolinamido)amide of the formula

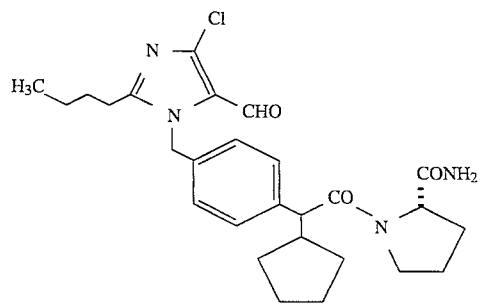

or an isomer or salt thereof.

8. An imidazolyl-substituted phenyl acetic acid prolinamide according to claim 1 wherein such compound is 2-[4-(2-Butyl-4 -chloro-5-carboxy-imidazol-1-yl-methyl)-phenyl]-2-cyclopentylacetic acid L-prolinamide of the formula

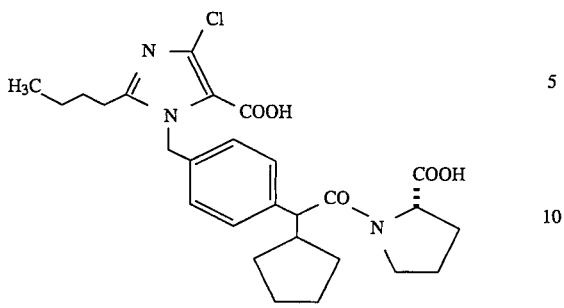

or an isomer or salt thereof.

9. An imidazolyl-substituted phenyl acetic acid prolinamide according to claim 1 wherein such compound is 2-[4-(2-Butyl-4 -chloro-5-carboxy-imidazol-1-yl-methyl)-phenyl]-2-cyclopentylacetic acid (L-prolinamido)amide of the formula

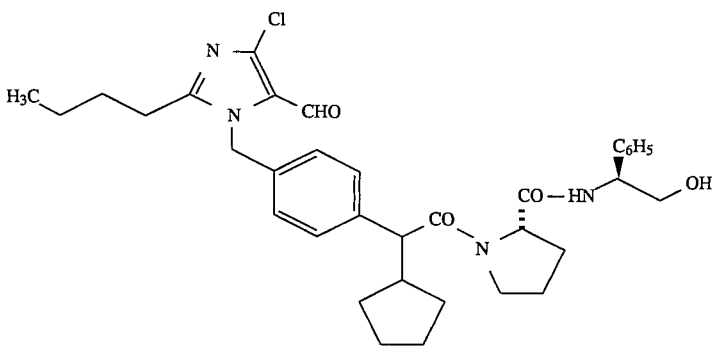

or an isomer or salt thereof.

10. An imidazolyl-substituted phenyl acetic acid prolinamide according to claim 1 wherein such compound is 2-[4-(2-Butyl-4 -chloro-5-hydroxymethyl-imidazol-1-yl-methyl)phenyl]-2 -cyclopentylacetic acid (L-prolinephenylglycinolamido)amide of the formula

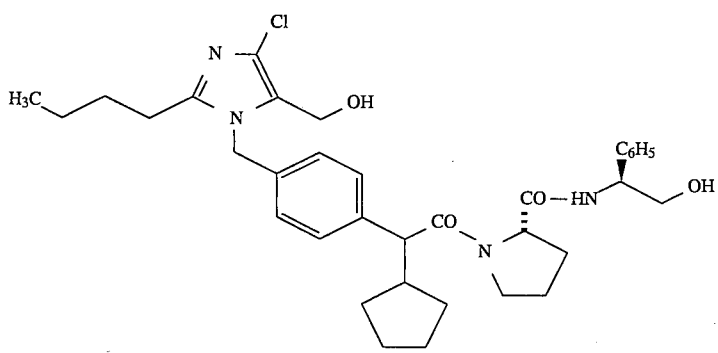

or an isomer or salt thereof.

11. A composition for the treatment of arterial hypertension and atherosclerosis comprising an amount effective therefore of a compound an isomer thereof or a salt thereof according to claim 1 and a pharmacologically acceptable diluent.

12. The method of treating arterial hypertension and atherosclerosis in a patient in need thereof which comprises administering to such patient an amount effective therefore of a compound an isomer thereof or a salt thereof according to claim 1.

* * * * *